(12) United States Patent
Ishino et al.

(10) Patent No.: US 7,285,294 B2
(45) Date of Patent: Oct. 23, 2007

(54) HAIR GROWTH INHIBITORS AND COMPOSITION CONTAINING SAME

(75) Inventors: Akihiro Ishino, Yokohama (JP); Tomoko Yokoyama, Yokohama (JP); Takanari Tsuda, Yokohama (JP); Chika Hamada, Yokohama (JP); Daigo Mizumoto, Yokohama (JP); Masahiro Tajima, Yokohama (JP)

(73) Assignee: Shiseido Company, Ltd., Tokyo (JP)

( * ) Notice: Subject to any disclaimer, the term of this patent is extended or adjusted under 35 U.S.C. 154(b) by 0 days.

(21) Appl. No.: 11/105,523

(22) Filed: Apr. 14, 2005

(65) Prior Publication Data

US 2005/0175576 A1    Aug. 11, 2005

Related U.S. Application Data

(63) Continuation of application No. 10/450,473, filed as application No. PCT/JP01/11300 on Dec. 21, 2001, now abandoned.

(30) Foreign Application Priority Data

Dec. 22, 2000   (JP)   .............................. 2000-390932
Apr. 5, 2001    (JP)   .............................. 2001-106658

(51) Int. Cl.
  *A01N 65/00*   (2006.01)
  *A61Q 7/02*    (2006.01)
  *A61K 36/71*   (2006.01)
  *A61K 36/78*   (2006.01)
  *A61K 8/00*    (2006.01)

(52) U.S. Cl. .......................... 424/725; 424/47; 424/74; 424/773; 424/779; 424/70.1

(58) Field of Classification Search .................... None
See application file for complete search history.

(56) References Cited

U.S. PATENT DOCUMENTS

| | | | |
|---|---|---|---|
| 4,525,344 A | 6/1985 | Tutsky | |
| 4,720,489 A | 1/1988 | Shander | |
| 5,648,394 A | 7/1997 | Boxall et al. | |
| 5,653,970 A | 8/1997 | Vermeer | |
| 5,674,497 A | 10/1997 | Kuwana et al. | |
| 6,113,926 A | 9/2000 | Soler et al. | |

FOREIGN PATENT DOCUMENTS

| | | | |
|---|---|---|---|
| CN | 1108567 A | | 9/1995 |
| DE | 44 34 312 A1 | | 3/1996 |
| EP | 0 339 634 | | 11/1989 |
| EP | 0 953 341 A2 | | 11/1999 |
| EP | 0 956 852 | | 11/1999 |
| FR | 2 546 405 | | 11/1984 |
| FR | 2 572 280 | | 5/1986 |
| GB | 0399007 A | * | 8/1932 |
| JP | 57-185210 | | 11/1982 |
| JP | 60-56911 A | | 4/1985 |
| JP | 1-256587 | | 10/1989 |
| JP | 05-279242 | | 10/1993 |
| JP | 8-81336 A | | 3/1996 |
| JP | 09-208431 | | 8/1997 |
| JP | 10-139639 A | | 5/1998 |
| JP | 10-175842 | | 6/1998 |
| JP | 10194935 A | * | 7/1998 |
| JP | 10-265341 | | 10/1998 |
| JP | 10-298055 | | 11/1998 |
| JP | 11-005719 | | 1/1999 |
| JP | 11-106321 | | 4/1999 |
| JP | 11-139942 | | 5/1999 |
| JP | 11-335235 | | 12/1999 |
| JP | 2000-063226 | | 2/2000 |
| JP | 2000-086486 | | 3/2000 |
| JP | 2000086449 A | * | 3/2000 |
| JP | 2000-327535 | | 11/2000 |
| JP | 2000-327555 | | 11/2000 |
| JP | 2001-261538 A | | 9/2001 |
| JP | 2001-316234 | | 11/2001 |
| JP | 2001-335414 A | | 12/2001 |
| WO | WO 02/43682 | | 6/2002 |

OTHER PUBLICATIONS

D.J. Mabberley, *The Plant-Book: A portable dictionary of the vascular plants.* Second Edition (1997) Cambridge University Press, United Kingdom, pp. 488, 600 and 601.

* cited by examiner

*Primary Examiner*—Michele Flood
(74) *Attorney, Agent, or Firm*—Snider & Associates; Ronald R. Snider

(57) ABSTRACT

A hair growth inhibitor contains, as an active ingredient, at least one herb selected from the group consisting of *phellodendron* bark, *houttuynia*, rice bran, mulberry tree bark, Japanese *coptis*, thyme, peach seed, nettle, *calendula*, wild rose and balm mint or the extract thereof and various skin external application compositions such as cosmetic compositions to be used on the outer skin is prepared by mixing these active ingredients with other aqueous phase ingredients and oil phase ingredients according to conventional methods.

7 Claims, No Drawings

HAIR GROWTH INHIBITORS AND COMPOSITION CONTAINING SAME

RELATED APPLICATIONS

This application claims the priority of Japanese Patent Application No. 2000-390932 filed on Dec. 22, 2000 and Japanese Patent Application No. 2001-106658 filed Apr. 5, 2001, which are incorporated herein by reference. This application is a continuation of U.S. patent application Ser. No. 10/450,473, filed Jun. 13, 2003, now abandoned a national stage of PCT/JP01/11300, filed Dec. 21, 2001.

TECHNICAL FIELD

The present invention relates to a hair growth inhibitor such as a hair development inhibitor containing a specific herb or its extract, as an active ingredient, and external application compositions such as a cosmetic, quasi-drug or skin lotion, particularly a cosmetic composition, containing the same.

BACKGROUND ART

The head hair or body hair of the human body inherently biologically protects important body organs such as head, chest, limbs, but means of protection such as clothing, protective means have appeared and are used and developed by human beings, the protective function of body hair is becoming no longer important.

Further, in general, while abundant head hair is still desirable, in recent years there has been an increasing trend favoring no body hair, particularly on the limbs, in terms of aesthetic appearance. Therefore, various hair removing methods have been developed and utilized. Specifically, mechanical removal methods using a shavers, hair depilators, etc., methods of using hair depilatory agents to remove body hair from their roots, methods of removal of body hair by chemical action using hair removal agents, etc. may be mentioned.

However, these hair removal methods are sometimes accompanied with physical or chemical irritation to the skin. Further, while there is some difference depending on the hair removal methods, there are limits to the sustainability of the hair removal effect. Therefore, the hair removal treatment must be repeated after the elapse of a certain time. Reduction of the hair removal treatment work is therefore desired.

As mentioned above, the development of technology, for example, for inhibiting the growth or removal of, body hair providing less irritation on the skin and capable of lightening the burden of hair removal treatment work is desired. Under these circumstances, the present inventors engaged in intensive research on the hair growth inhibiting abilities of various herbs and found that specific herbs have hair growth inhibiting capability. As a result, we succeeded in the development of the hair growth inhibitor according to the present invention and cosmetics and external application compositions such as a cosmetic composition containing the same.

DISCLOSURE OF INVENTION

Accordingly, the object of the present invention is to provide a hair growth inhibitor capable of effectively inhibiting the growth or development of body hair and reduce the number of times of hair removal treatment and external application compositions such as a cosmetic composition containing the same. In particular, the present invention found that specific herbs or the extracts thereof act directly on hair matrix cells and dermal papilla cells to provide a superior hair growth inhibiting effect and have high safety over long term use and provides a hair growth inhibitor having one of these herbs or the extracts thereof as an active ingredient and external application compositions such as a cosmetic composition containing the same.

In accordance with the present invention, there are provided a hair growth inhibitor comprising, as an active ingredient, at least one herb selected from the group consisting of *phellodendron* bark, *houttuynia*, rice bran, mulberry tree, bark, Japanese *coptis*, thyme, peach seed, nettle, *calendula*, wild rose and balm mint or the extract thereof and an external application composition such as a cosmetic composition containing the same.

MODE FOR CARRYING OUT THE INVENTION

As explained above, the hair growth inhibitor according to the present invention uses, as an active ingredient, one or two or more herbs selected from *phellodendron* bark, *houttuynia*, rice bran, mulberry bark, Japanese *coptis*, thyme, peach seed, nettle, *calendula*, wild rose and balm mint or the extracts thereof. This active ingredient is the herb itself or the extract thereof. Each herb selected from *phellodendron* bark, *houttuynia*, rice bran, mulberry bark, Japanese *coptis*, thyme, peach seed, nettle, *calendula*, wild rose and balm mint may be directly used as it is in the form of the entire plant or one or two or more parts of the roots, fruit, seeds, and flower (hereinafter called the "original form") or may be used in the form of an extract. Note that the above herbs and herb extracts may be used alone or in combinations of any two or more types thereof.

The extract of the herb used in the present invention means various types of solvent extract solutions obtained by extracting the above-mentioned herbs with a solvent at ordinary temperature or under heating or extraction using Soxhlet extractor extraction devices such as a their dilutions, their concentrates or their dried powders.

The herb extracts obtained by the above extraction methods may be directly used as extraction solutions as active ingredients of the hair growth inhibitor of the present invention, but may also be used by diluting, concentrating or freeze drying the extracts, followed by preparing powders or pastes. Further, in the present invention, extracts obtained by removing inert inclusions by techniques such as liquid-liquid distribution may be used.

The extracts of the herbs explained above may be obtained by ordinary methods. That is, it is possible to use the above-mentioned techniques or devices to impregnate or to heat under reflux the medicines together with the extraction solvents, then filter and concentrate the results. As the extraction solvents therefor, it is possible to use any solvents normally used for extraction of herbs.

As the extraction solvents, for example, water, alcohols such as methanol, ethanol, propylene glycol, 1,3-butylene glycol, glycerin, aqueous alcohols, organic solvents such as chloroform, dichloroethane, carbon tetrachloride, acetone, ethyl acetate, hexane, etc. may be mentioned. These may be used alone or in any combination thereof. Note that the extraction conditions may be made the conventional general conditions. Typically, the extraction may be performed under conditions of 20° C. for 1 to 10 days or 60 to 100° C. for 2 hours to 3 days.

The extracted solutions obtained by extraction with these solvents may be used, as they are or after concentration, or after removal of impurities by adsorption, for example, using an ion exchange resin, or may be adsorbed in a porous polymer (e.g., Amberlite XAD-2) column, eluted with methanol or ethanol, and concentrated. Further, an extract extracted by the distribution method, for example, water/ ethyl acetate, may also be used.

The plant extracts thus obtained have superior hair growth inhibiting effects as explained above and as shown by the results of tests on inhibition of proliferation of rat follicular epithelial cells explained below and the results of tests on inhibiting hair development explained below and have been used for the human body over long years in Chinese herbal medicines etc., and therefore, are high safety. As explained above, these plant extracts can be suitably used as active ingredients for hair growth inhibitors and, further, these hair growth inhibitors can be used as ingredients giving hair growth inhibiting performance to various external application compositions such as cosmetics, drugs in the form of skin lotions.

The above herbs and their extracts are preferably contained in amounts of 0.000001 to 5% by weight in terms of dry weight, more preferably 0.00001 to 3% by weight, particularly 0.00001 to 1% by weight, based upon the total weight the external application compositions.

The above herbs and their extracts are used as active ingredients together with bases in skin external application compositions such as cosmetics, having hair growth inhibiting performance, but in addition to these active ingredients, it is possible to suitably formulate as the bases and additives, in such a range that the effect of the present invention is not impaired, optionally, other ingredients normally used in cosmetics or drugs or other skin lotions, for example, oils, moisturizers, UV absorbers, antioxidants, surfactants, preservatives, humectants, fragrances, water, alcohol, thickening agents, etc.

As the UV absorbers, benzophenone derivatives such as 2-hydroxy-4-methoxybenzophenone, sodium 2-hydroxy-4-methoxybenzophenon-5-sulfonate, sodium benzotriazolylbutylphenol sulfonate, methylene bis-benzotriazolyltetramethylbutylphenol; methoxycinnamic acid derivatives such as octyl p-methoxycinnamate, glyceryl di-p-methoxycinnamate mono-2-ethylhexanoate, trisiloxane isopentyltrimethoxycinnamate, urocanic acid, 4-tert-4'-methoxydibenzoylmethane, bis-ethylhexyloxyphenolmethoxyphenyltriazine, ethylhexyltriazone, phenylbenzimidazole sulfonic acid, etc. may be suitably formulated, if needed.

Further, in addition to the other ingredients used for the above-mentioned skin lotion compositions, metal ion sequestering eggents such as disodium edetate, trisodium edetate, sodium citrate, sodium polyphosphate, sodium metaphosphate, gluconic acid, medicines such as caffeine, tannin, verapamil, tranexemic acid and its derivatives, glycyrrhiza extract, glabrazine, various herbs, tocopheryl acetate, glycyrrhizinic acid and its derivatives or its salts, vitamin C, magnesium L-ascorbyl-2-phosphate, ascorbyl glucoside, albutin, kojic acid, resorcinol, ellagic acid, matricaria extract, saccharides such as glucose, fructose, mannose, sucrose, trehalose, etc. may be further suitably formulated.

Further, the hair growth inhibitor of the present invention may be used for formulating into a cosmetic, drug, quasi-drug, etc. to be applied to the skin. In particular, it may be suitably widely used for cosmetics. It may be of any form which is able to be applied to the skin. A solution system, solubilizable system, emulsion system, powder dispersion system, water-oil double two system, water-oil-powder three layer system, ointment, gel, aerosol or any other form may be employed.

Further, the product of the external application composition such as a cosmetic composition, in which the hair growth inhibitor of the present invention is formulated may be of any type. For example, it may be made lotion, milky lotion, cream, face pack or other facial cosmetic compositions, or a foundation. In addition, it is possible to use it for makeup cosmetic composition, fragrance cosmetic, bath preparation, etc. Note that the form and the type of product which the external application composition such as the cosmetic composition in which the hair growth inhibitor of the present invention is formulated may take are of course not limited to the specific forms and types of products listed above.

As preferable types of products of the cosmetic composition in which the hair growth inhibitor of the present invention is formulated, there are hair removal, hair depilation, or shaving related cosmetics, but the present invention is not particularly limited thereto. As specific products of such cosmetics, paste, cream, aerosol, and other hair removers, wax, gel, sheet, and other hair depilatory, lotions, creams, or other after-treatment agents used for treatment after hair removal or hair depilatory, deodorant lotions, deodorant powders, deodorant sprays, deodorant sticks, and other sweat suppressing and deodorizing products, pre-shaving lotions and other pre-shaving treatment products, shaving creams and other shaving agents, after-shaving lotions and other after-treatment products, etc. may be mentioned.

Note that the form, type of product, and specific product of the external application composition such as the cosmetic composition in which the hair growth inhibitor of the present invention is formulated are of course not limited to the above-mentioned specific forms, types of products and specific products.

EXAMPLES

The present invention will now be explained in further detail by Production Examples of the hair growth inhibitor of the present invention and Evaluation Tests of the hair growth inhibiting performance using the hair growth inhibitors produced, but the present invention is not limited in any way by these production examples and inhibiting performance evaluation tests and is only specified by the description in the claims. Note that in the following Examples, the amounts of the herbs or herb extracts formulated are shown in terms of dry solid content. Further, the "%", unless otherwise particularly indicated, is "% by weight".

Production Example 1

Preparation of *Houttuynia Cordata* Extract 200 g of the above ground part of *houttuynia* (*Houttuynia cordataThunb.*) in the flowering season (dried product) was immersed in 3 liters of 50% ethanol and extracted for one day. The solvent (i.e., ethanol) was then distilled off from the extraction solution to obtain 13.5 g of the extract.

Production Example 2

Preparation of *Houttuynia Cordata* Extract 240 g of the above ground part of *houttuynia* (*Houttuynia cordataThunb.*) in the flowering season (dried product) was immersed in 1.7 liters of 100% ethanol and extracted at 80 to 85° C. for 2 hours. The ethanol was then distilled off from the extraction solution to obtain 15.9 g of the extract.

Production Example 3

Preparation of *Phellodendron* Bark Extract 200 g of the Japanese Pharmacopoeia "*Phellodendron* Bark" (bark of *Phellodendron amrense R.* except periderm) was immersed in 2 liters of 70% ethanol and extracted for three days. The solvent was then distilled off from the extraction solution to obtain 18.9 g of the extract.

Production Example 4

Preparation of Rice Bran Extract 240 g of rice-bran extract was immersed in 2 liters of 100% ethanol and extracted at 80 to 85° C. for 2 hours. The ethanol was then distilled off from the extraction solution to obtain 12.9 g of the extract.

Production Example 5

Preparation of Mulberry Bark Extract 100 g of the bark of the mulberry tree (*Morus Bombycis* KOIDZ) was immersed in 3 liters of 100% ethanol and extracted at room temperature for 2 days. The ethanol was then distilled off from the extraction solution to obtain 14.9 g of the extract.

Production Example 6

Preparation of Japanese *Coptis* Extract 300 g of the root and stem of Japanese *coptis* (*Coptis japonic* MAKINO) was immersed in 3 liters of 100% methanol and extracted at room temperature for two days. The methanol was then distilled off from the extraction solution to obtain 16.9 g of the extract.

Production Example 7

Preparation of Thyme Extract 300 g of the entire plant of wild thyme of the *Lamiaceae* (*Thymus serpyllum L.*) was immersed in 2 liters of 80% ethanol and extracted at room temperature for 10 days. The solvent was then distilled off from the extraction solution to obtain 16.3 g of the extract.

Production Example 8

Preparation of Peach Seed Extract 300 g of seeds of peaches of the *Rosaceae* (*Prunus persica B.*) was immersed in 3 liters of 30% ethanol and extracted at room temperature for 10 days. The solvent was then distilled off from the extraction solution to obtain 20.3 g of the extract.

Production Example 9

Preparation of Nettle Extract 300 g of the entire plant of nettle of the was immersed in 3 liters of 30% ethanol and extracted at 60 to 80° C. for two days. The solvent was then distilled off from the extraction solution to obtain 24.3 g of the extract.

Production Example 10

Preparation of *Calendula Officinalis* Flower Extract 300 g of the flower of the *calendula* of the *Compositeae* (*Calendula officinalis L.*) was immersed in 3 liters of 50% ethanol and extracted at 60 to 80° C. for two days. The solvent was then distilled off from the extraction solution to obtain 19.3 g of the extract.

Production Example 11

Preparation of Wild Rose Extract 200 g of the leaves of the wild rose of the *Rosaceae* (*Rose canica L.*) was immersed in 2 liters of 50% ethanol and extracted at room temperature for 10 days. The solvent was then distilled off from the extraction solution to obtain 22.3 g of the extract.

Production Example 12

Preparation of Balm Mint Extract 200 g of the leaves of the balm mint of the *Lamiaceae* (*Melissa officinalis L.*) was immersed in 2 liters of 50% ethanol and extracted at 60 to 80° C. for two days. The solvent was then distilled off from the extraction solution to obtain 28.3 g of the extract.

Hair Growth Inhibiting Performance Evaluation Test

An evaluation test was performed using the body hair cells of rats to evaluate the hair growth inhibiting performance. Details of the test are given below. Note that rat body hair cells were taken with reference to the method described in Japanese Unexamined Patent Publication (Kokai) No. 10-265341.

A. Test on Inhibiting Proliferation of Rat Follicular Epithelial Cells

1. Preparation of Rat Follicular Epithelial Cells (1) Preparation of Follicles

Dorsal skin was taken from newborn (3 to 4 day old) rats and immersed overnight in 0.25% trypsin-containing PBS (including 0.02% EDTA, same below) at 4° C.

After immersion, the dermis layer and the epidermis layer of the dorsal skin were separated, the dermis layer was cut by scissors, then steeped at 37° C. for 35 minutes in a Ham's F12 medium containing 0.35% collagenase. After permeation, this was pipetted until clump-like masses were no longer seen in the collagenase reaction product, then Ham's F12 medium containing DNase (10000 units) was added and allowed to stand for 5 minutes.

After standing, the suspension obtained was further pipetted, then filtered by a Nylon mesh (Nytex 157 mesh), then the suspension was diluted by PBS (−) and centrifuged (4°

C., 400 rpm, 5 minutes). After centrifuging, the supernatant was removed and PBS (−) was added to the residue to cause resuspension, then the resultant suspension was further centrifuged [(4° C., 400 rpm, 5 minutes)×3 times]. The residue obtained from this centrifugation operation was the follicles in the dorsal skin of rats to thereby prepare the follicles.

(2) Preparation of Follicular Epithelial Cells 0.25% trypsin-containing PBS (−) was added to the follicles obtained by the above operation. The cell suspension was then incubated at 37° C. for 5 minutes. After the end of the incubation, equal amounts of fetal bovine serum (FBS) and Ham's F12 medium were added, then the cell suspension was filtered by a cell strainer (100 μm, made by Nalgene). After filtration, the filtrate was centrifuged (4° C., 1500 rpm, 5 minutes). The supernatant was removed from the filtrate after centrifugation to obtain the desired follicular epithelial cells as the residue.

2. Preculturing of Follicular Epithelial Cells

To remove, as much as possible, the fibroblasts contained in, the follicular epithelial cells obtained above were precultured. This procedure will be explained below.

The number of cells of the follicular epithelial cells obtained was calculated by a hemocytometry plate and adjusted by an FAD medium to give a concentration of $2.5 \times 10^5$ cells/ml. The above cells were inoculated in a 75 $cm^2$ flask coated with I-type collagen and cultured overnight at 37° C. in 5% $CO_2$. After culturing, the resultant product was washed two times with 10 ml of PBS (−), 2 ml of 0.25% trypsin-containing PBS (−1) was added, then the resultant cells were incubated at 37° C. in 5% $CO_2$ for 4 minutes. Next, 2 ml of fetal bovine serum (FBS) was added, the resultant mixture was lightly shaken, then the supernatant was separated. This removed the fibroblasts contained therein.

Further, after the separation of the supernatant, 15 ml of KGM medium [Keratinocyto growth medium: medium comprised of keratinocyto basal medium (KBM medium (modified MCD153 medium (made by Clonetics)) plus bovine pituitary extract ((BPE) 0.4 vol %), insulin (0.5 μm/ml), hydrocortisone (0.5 μm/ml), h-EGF (0.1 ng/ml), same below] was added, then the resultant mixture was cultured at 37° C. in 5% $CO_2$ for three days.

B. Preparation of Test Samples

1. Preparation of Test Samples for Medium

The herb extracts obtained from Production Examples 1 to 6 were adjusted by DMSO to give 0.2% solutions. Further, as a control, a 70% ethanol extract of coriander seeds (*Coriandrum sativum L.*) with a known hair development effect was adjusted by DMSO to give a 0.2% solution and diluted by KGM medium to prepare a test sample for a medium for use for evaluation.

2. Preparation of Control Medium

KGM medium was used for evaluation as a control.

3. Assay of Substance to be Tested

The rate of intermixture of fibroblasts (FB intermixture rate) of a culturing flask inoculated with the follicular epithelial cells obtained by the above operation was measured (×300, 5 observation fields). Samples with FB intermixture rates of 3% or more were excluded from the coverage of the assay. The follicular epithelial cells were washed two times by 10 ml of PBS (−), 0.25% trypsin-containing PBS (−) was added, then the result was shaken at 37° C. at 20 rpm for 5 minutes.

The suspension formed by the above shaking operation was filtered by a cell strainer (100 μm, made by Nalgene). After filtration, 50 ml was placed in a centrifugation tube, the number of live cells in the suspension was calculated by a hemocytometry plate, then KGM medium was added to the suspension to adjust it to a cell concentration of $5.0 \times 10^4$ cells/ml. Next, the adjusted suspension was inoculated in a 96-well plate (I-type collagen coated plate, made by Falcon) in an amount of 0.2 ml/well ($1.0 \times 10^4$ cells/well), then cultured at 37° C. in 5% $CO_2$ for one day. The media were exchanged in the control medium (KGM medium) and test samples, then the resultant mixtures were incubated at 37° C. in 5% $CO_2$ for two days. After this, the cell proliferation was measured by the following method. The results are shown in Table I.

C. Measurement of Cell Proliferation

A 1/10 amount of alamar blue (made by Alamar Bioscience) was added based upon the culturing amount (volume) and the resultant mixture was incubated at 37° C. (5% $CO_2$) for 6 hours. After incubation, the absorbances of the system at 595 nm and 570 nm were measured using a micro plate reader (made by Bio RAD).

D. Judgment of Results

In the two days after the exchange of the medium, the number of the rat follicular epithelial cells in the control KGM medium proliferated about two-fold. Using the degree of cell proliferation in the control medium as 100%, the degree of cell proliferation at the time of addition of each sample was measured. The difference between the former and the latter was calculated and used as the cell proliferation inhibiting rate.

E. Inhibiting Effect Judgment Criteria

The inhibiting effect was judged by the following judgment criteria:

| | | |
|---|---|---|
| Proliferation inhibited 20% or more | Strong inhibiting effect | ⊙ |
| Proliferation inhibited 10% to less than | Inhibiting effect | ○ |
| Proliferation inhibited less than 10% | Weak inhibiting effect | Δ |
| Proliferation inhibited −5% or less | Promoting effect | X |

TABLE I

| Sample | Concentration (%) | Degree of proliferation (%) | Proliferation inhibiting rate (%) | Judgment |
|---|---|---|---|---|
| Control | | 100 | 0 | |
| Houttuynia extract (Production Example 1) | 0.00001 | 95 | 5 | Δ |
| | 0.0001 | 89 | 11 | ○ |
| | 0.001 | 77 | 23 | ⊙ |
| | 0.01 | 73 | 27 | ⊙ |
| | 0.1 | 68 | 32 | ⊙ |
| Houttuynia extract (Production Example 2) | 0.00001 | 98 | 2 | Δ |
| | 0.0001 | 92 | 8 | Δ |
| | 0.001 | 86 | 14 | ○ |
| | 0.01 | 80 | 20 | ⊙ |
| Phellodendron bark | 0.00001 | 97 | 3 | Δ |
| | 0.0001 | 90 | 10 | ○ |

TABLE I-continued

| Sample | Concentration (%) | Degree of proliferation (%) | Proliferation inhibiting rate (%) | Judgment |
|---|---|---|---|---|
| (Production Example 3) | 0.001 | 83 | 17 | ○ |
| | 0.01 | 78 | 22 | ◎ |
| Rice bran extract (Production Example 4) | 0.00001 | 95 | 5 | Δ |
| | 0.0001 | 90 | 10 | ○ |
| | 0.001 | 85 | 15 | ○ |
| | 0.01 | 79 | 21 | ◎ |
| Mulberry tree bark extract (Production Example 5) | 0.00001 | 92 | 8 | Δ |
| | 0.0001 | 88 | 12 | ○ |
| | 0.001 | 83 | 17 | ○ |
| | 0.01 | 77 | 23 | ◎ |
| Japanese coptis extract (Production Example 6) | 0.00001 | 92 | 8 | Δ |
| | 0.0001 | 89 | 11 | ○ |
| | 0.001 | 86 | 14 | ○ |
| | 0.01 | 80 | 20 | ◎ |
| Coriander extract (control example) | 0.00001 | 102 | −2 | — |
| | 0.0001 | 106 | −6 | X |
| | 0.001 | 110 | −10 | X |
| | 0.01 | 113 | −13 | X |

As is clear from the results of the above hair growth inhibiting performance evaluation tests, in the evaluation tests based on rat follicular epithelial cells using the herb extracts of the active ingredients of the hair growth inhibitor of the present invention, the extracts of Production Examples 1 to 6 were observed to have hair growth inhibiting effects C3H Mouse Hair Development Inhibiting Test The dorsal hairs of groups of three C3H mice of eight weeks age were shaved off by electrical shears over 2×4 cm² areas, then surface hair removal cream (Shiseido: Devenu) was used for treatment to remove surface hair. The test samples were coated over the surface hair removal portions once a day in amounts of 100 µl a time over 18 days. The test samples were dissolved in a solvent (100% ethanol). For the control group, only the solvent was coated.

The hair recovery of the surface hair-removal portions 10 days and 18 days after coating were scored. The hair development inhibiting effects were compared with the control growth for the scores 10 days after coating. Scores of points lower than the control growth were evaluated as indicating there were hair developing inhibiting effects. The growth inhibiting effects were evaluated by finding the difference of the scores for 10 days and 18 days after coating and judging differences smaller than the difference of the control group as growth inhibiting effects. The concentrations of the test samples and the results of evaluation are shown in Table III.

TABLE II

| Points | State of hair recovery |
|---|---|
| 0 | No hair development |
| 1 | Skin of surface hair removal portion becomes black |
| 2 | Tips of hairs visible |
| 3 | Hairs of lengths about half of those of non-surface hair removal portions observed |
| 4 | Covered by hairs of same lengths as non-surface hair removal portions |

Each mouse evaluated for hair recovery in increments of 0.5 point.

TABLE III

| Test sample | Concentration (wt %) | Hair recovery evaluation points (average for 3 mice) | | | Evaluation | |
|---|---|---|---|---|---|---|
| | | 10 days | 18 days | Difference (18 day − 10 day) | Hair development inhibition | Growth inhibition |
| Solvent (EtOH) | | 0.67 | 3.67 | 3.0 | — | — |
| Houttuynia extract | 0.01 | 0.5 | 2.83 | 2.33 | Yes | ○ |
| Thyme extract | 0.01 | 0.33 | 2.17 | 1.84 | Yes | ◎ |
| Calendula extract | 0.01 | 0.67 | 2.17 | 1.5 | | |
| Wild rose extract | 0.01 | 0.5 | 3.5 | 3.0 | Yes | ◎ |
| Balm mint extract | 0.01 | 0.67 | 2.83 | 2.16 | | ○ |
| Peach seed extract | 0.01 | 0.33 | 2.83 | 2.5 | Yes | Δ |
| Nettle extract | 0.01 | 0.33 | 2.33 | 2.00 | Yes | ○ |
| Japanese coptis extract | 0.01 | 0.33 | 3.0 | 2.67 | Yes | Δ |

(Note)
Note that for example the Houttuynia extract has been confirmed by tests to be effective for human beings as well.

Note that these judgment criteria may be explained in further detail as follows:

Hair Development Inhibiting Effect

Yes: Value of "hair recovery evaluation points" on 10th day lower than "0.67" of value of "Solvent (EtOH)"

Growth Inhibiting Effect

◎: (Strong) Difference of scores of 10 days and 18 days after coating less than 2

○: Difference of scores of 10 days and 18 days after coating 2 or more but less than 2.5

Δ: Difference of scores of 10 days and 18 days after coating less than 3

The active ingredients used in the above Tests, that is, the herbs or their extracts, and the concentrations of the same are shown in Table III. Further, the results of the evaluations are also shown in Table III. According to the results, houttuynia, thyme, wild rose, peach seed, nettle, and Japanese coptis extracts were observed to have hair development inhibiting effects. Further, houttuynia, thyme, calendula, balm mint, peach seed, nettle, and Japanese coptis extracts were observed to have growth inhibiting effects.

Examples of formulation of various preparations and specific methods of preparation of the same will be given as examples for the cosmetics of the present invention containing hair growth inhibitors of the present invention having herb extracts as active ingredients.

Example 1

Vanishing Cream

| Ingredients | wt % |
|---|---|
| (1) Stearic acid | 6.0 |
| (2) Sorbitan monostearic acid ester | 2.0 |

-continued

| Ingredients | wt % |
|---|---|
| (3) Polyoxyethylene (20) sorbitan monostearic ester | 1.5 |
| (4) Albutin | 7.0 |
| (5) Sodium bisulfite | 0.03 |
| (6) Propylene glycol | 7.0 |
| (7) Glycerin | 3.0 |
| (8) *Houttuynia* extract (Production Ex. 1) | 1.0 |
| (9) Ethyl parabene | 0.1 |
| (10) Butyl parabene | 0.1 |
| (11) Thiourea | 0.01 |
| (11) Fragrance | 1.0 |
| (13) Ion exchange water | Bal. |

Preparation Method

The ingredients (4), (6), (7), and (8) were added to the ingredient (13), then the resultant mixture was heated and held at 70° C. to form an aqueous phase. On the other hand, the ingredients (1) to (3), (5), and (9) to (12) were mixed, heated to melt, then held at 70° C. to form an oil phase. The oil phase was added to the aqueous phase and preemulsified, then the resultant mixture was homogeneously emulsified by a homomixer, then cooled down to 30° C., while stirring vigorously to obtain a vanishing cream.

Example 2

Neutral Cream

| Ingredients | wt % |
|---|---|
| (1) Stearyl alcohol | 5.0 |
| (2) Stearic acid | 2.0 |
| (3) Hydrated lanolin | 2.0 |
| (4) 2-hydroxy-4-methoxybenzophenon | 2.0 |
| (5) Squalane | 5.0 |
| (6) 2-octyldodecyl alcohol | 6.0 |
| (7) Polyoxyethylene (25) cetyl alcohol ether | 3.0 |
| (8) Glyceryl monostearic ester | 2.0 |
| (9) Placenta extract | 0.1 |
| (10) Propylene glycol | 2.0 |
| (11) 1,3-butylene glycol | 3.0 |
| (12) Rice bran extract (Production Ex. 4) | 5.0 |
| (13) Fragrance | 0.2 |
| (14) 1,2-pentadiol | 0.5 |
| (15) Butyl parabene | 0.1 |
| (16) Hypotaurin | 0.01 |
| (17) Ion exchange water | Bal. |

Preparation Method

The ingredients (9) to (12) and (16) were added to the ingredient (17), then the resultant mixture was heated and held at 70° C. to form an aqueous phase. On the other hand, the ingredients (1) to (8) and (13) to (15) were mixed, heated to melt, then held at 70° C. to form an oil phase. The oil phase was added to the aqueous phase and preemulsified, then the resultant mixture was homogeneously emulsified by a homomixer, then cooled down to 30° C. while stirring vigorously to obtain a neutral cream.

Example 3

Cold Cream

| Ingredients | wt % |
|---|---|
| (1) Solid paraffin | 5.0 |
| (2) Beeswax | 5.0 |
| (3) Vaseline | 5.0 |
| (4) Liquid paraffin | 20.0 |
| (5) Squalane | 10.0 |
| (6) Glyceryl monostearic ester | 2.0 |
| (7) Polyoxyethylene (20) sorbitan monolauric ester | 2.0 |
| (8) Kojic acid | 2.0 |
| (9) Sodium 2-hydroxy-4-methoxybenzophenon-5-sulfonate | 3.5 |
| (10) Soap powder | 0.1 |
| (11) Borax | 0.2 |
| (12) Mulberry tree bark extract (Production Ex. 5) | 0.1 |
| (13) Ion exchange water | Bal. |
| (14) Fragrance | 0.2 |
| (15) Ethyl parabene | 0.2 |
| (16) Butyl parabene | 0.1 |
| (17) Butyl hydroxytoluene | 0.05 |

Preparation Method

The ingredients (8) and (10) to (12) were added to the ingredient (13), then the resultant mixture was heated and held at 70° C. to form an aqueous phase. On the other hand, the ingredients (1) to (7), (9), and (14) to (17) were mixed, heated to melt, then held at 70° C. to form an oil phase. The oil phase was gradually added to the aqueous phase while stirring to cause a reaction. After the end of the reaction, the resultant mixture was homogeneously emulsified by a homomixer, then cooled down to 30° C. while stirring vigorously to obtain a cold cream.

Example 4

Enriching Cream

| Ingredients | wt % |
|---|---|
| (1) Dimethyldistearyl ammonium hectonite | 2.0 |
| (2) Polyoxyethylene-methyl polysiloxane polymer | 0.1 |
| (3) Liquid paraffin | 10.0 |
| (4) Vaseline | 5.0 |
| (5) Methyl octanate | 20.0 |
| (6) Sodium L-glutamate | 0.01 |
| (7) Dipropylene glycol | 5.0 |
| (8) Methyl parabene | 0.2 |
| (9) Sodium hyaluronate | 0.05 |
| (10) Vitamin E acetate | 0.02 |
| (11) *Houttuynia* extract (Production Ex. 2) | 5.0 |
| (12) Ion exchange water | Bal. |

Preparation Method

The ingredients (2), (3), and (5) were raised in temperature to 50° C., then the ingredients (4) and (1) were added to completely melt the same. The ingredient (1) was added to this oil phase part and homogeneously dispersed. An aqueous phase part obtained by dissolving the ingredients (6), (7), (8), (9), and (11) in the ingredient (12) was added to the dispersion obtained, then was homogeneously dispersed by a homomixer. The resultant mixture was cooled down to room temperature to obtain a water-in-oil type emulsion composition.

Example 5

Milky Lotion

| Ingredients | wt % |
| --- | --- |
| (1) Polyoxyethylene (10) monooleic ester | 2.0 |
| (2) Octyl paramethoxycinnamate | 3.5 |
| (3) Liquid paraffin | 2.0 |
| (4) Cyclopentadimethylsiloxane | 1.0 |
| (5) Squalane | 3.0 |
| (6) 1,3-butylene glycol | 5.0 |
| (7) Albutin | 2.0 |
| (8) Sodium bisulfite | 0.03 |
| (9) Glycerin | 2.0 |
| (10) Ethanol | 5.0 |
| (11) Carboxyvinyl polymer | 0.3 |
| (12) Hydroxypropyl cellulose | 0.1 |
| (13) Sodium hydroxide | 0.15 |
| (14) Ethyl parabene | 0.1 |
| (15) 1,2-pentadiol | 1.0 |
| (16) Japanese coptis extract (Production Ex. 6) | 5.0 |
| (17) Ion exchange water | Bal. |
| (18) Fragrance | 0.3 |

Preparation Method

The ingredients (16) and (7) were warmed to melt in the ingredient (17) and ingredient (10) and then the ingredients (6), (8), (9), and (11) to (13) were dissolved and the resultant mixture held at 70° C. to form an aqueous phase. On the other hand, the ingredients (1) to (5), (14), (15), and (18) were mixed and heated to melt and held at 70° C. to obtain an oil phase. The oil phase was added to the aqueous phase and preemulsified, then the resultant mixture was homogeneously emulsified by a homomixer, then cooled down to 30° C. while stirring vigorously to obtain a milky lotion.

Example 6

Milky Lotion

| Ingredients | wt % |
| --- | --- |
| (1) Polyoxyethylene (20) polyoxy propylene (2) cetyl alcohol | 1.0 |
| (2) Octyl p-methoxycinnamate | 3.5 |
| (3) "Silicone KF96" (20 cs) (made by Shin-Etsu Chemical) | 2.0 |
| (4) Liquid paraffin (medium viscosity) | 3.0 |
| (5) 4-tert-butylmethoxydibenzoyl methane | 0.3 |
| (6) Glyceryl tri-2-ethylhexanoate | 1.0 |
| (7) Albutin | 2.0 |
| (8) Sodium bisulfite | 0.03 |
| (9) Glycerin | 2.0 |
| (10) Ethanol | 3.0 |
| (11) Carboxyvinyl polymer | 0.3 |
| (12) Hydroxypropyl cellulose | 0.1 |
| (13) Sodium hydroxide | 0.1 |
| (14) 1,2-pentadiol | 2.0 |
| (15) Phenoxyethanol | 0.2 |
| (16) Phellodendron bark extract (Production Ex. 3) | 5.0 |
| (17) Ion exchange water | Bal. |

Preparation Method

The ingredients (16) and (7) were warmed to melt in the ingredient (17) and ingredient (10) and then the ingredients (6), (8), (9), (11) to (13), and (15) were dissolved and the resultant mixture held at 70° C. to form an aqueous phase. On the other hand, the ingredients (1) to (5) and (14) were mixed and heated to melt and held at 70° C. to obtain an oil phase. The oil phase was added to the aqueous phase and preemulsified, then the result was homogeneously emulsified by a homomixer, then cooled down to 30° C., while stirring vigorously to obtain a milky lotion.

Example 7

Milky Lotion

| Ingredients | wt % |
| --- | --- |
| (1) Polyoxyethylene (20) polyoxy propylene (2) cetyl alcohol | 1.0 |
| (2) Glyceryl p-methoxycinnamic acid mono-2-ethylhexanoate | 2.0 |
| (3) "Silicone KF96 (20 cs) (made by Shin-Etsu Chemical) | 2.0 |
| (4) Squalane | 3.0 |
| (5) 1,3-butylene glycol | 5.0 |
| (7) Ascorbic acid-2-glucoside | 3.0 |
| (7) Polyethylene glycol 400 | 3.0 |
| (8) Glycerin | 2.0 |
| (9) Ethanol | 5.0 |
| (10) Carboxyvinyl polymer | 0.3 |
| (11) Hydroxypropyl cellulose | 0.1 |
| (12) Sodium hydroxide | 0.1 |
| (13) Butyl parabene | 0.1 |
| (14) Phenoxyethanol | 0.4 |
| (15) Thiourea | 0.02 |
| (16) *Houttuynia* extract (Production Ex. 1) | 2.0 |
| (17) Ion exchange water | Bal. |
| (18) Fragrance | 0.1 |

Preparation Method

The ingredients (15), (16), and (6) were dissolved in the ingredient (17) and ingredient (9) and then the ingredients (5), (7), (8), (10) to (12), and (14) were dissolved and the resultant mixture held at 70° C. to form an aqueous phase. On the other hand, the ingredients (1) to (4), (13), and (18) were mixed and heated to melt and held at 70° C. to obtain an oil phase. The oil phase was added to the aqueous phase and preemulsified, then the resultant mixture was homogeneously emulsified by a homomixer, then cooled down to 30° C. while stirring vigorously to obtain a milky lotion.

Example 8

Milky Lotion

| Ingredients | wt % |
| --- | --- |
| (1) Polyoxyethylene (20) polyoxy propylene (2) cetyl alcohol | 1.0 |
| (2) "Silicon KF96" (20 cs) (made by Shin-Etsu Chemical) | 2.0 |
| (3) Liquid paraffin (medium viscosity) | 3.0 |
| (4) Methylenebis-benzotriazolyl tetramethylbutylphenol | 1.0 |
| (5) 1,3-butylene glycol | 5.0 |
| (6) Glycerin | 2.0 |
| (7) Ethanol | 4.0 |
| (8) Carboxyvinyl polymer | 0.3 |

-continued

| Ingredients | wt % |
|---|---|
| (9) Hydroxypropyl cellulose | 0.1 |
| (16) Sodium hydroxide | 0.05 |
| (11) 1,2-pentadiol | 1.0 |
| (12) Butyl parabene | 0.1 |
| (13) Kojic acid | 3.0 |
| (14) *Houttuynia* extract (Production Ex. 2) | 3.0 |
| (15) Ion exchange water | Bal. |

Preparation Method

The ingredient (13) was heated to dissolve in the ingredient (15), then the ingredient (14) and the ingredients (14) and (5) to (10) were dissolved and the resultant mixture held at 70° C. to form an aqueous phase. On the other hand, the ingredients (1) to (4), (11), and (12) were mixed and heated to melt and held at 70° C. to obtain an oil phase. The oil phase was added to the aqueous phase and preemulsified, then the resultant mixture was homogeneously emulsified by a homomixer, then cooled down to 30° C., while stirring vigorously to obtain a milky lotion.

Example 9

Milky Lotion

| Ingredients | wt % |
|---|---|
| (1) Stearic acid | 1.5 |
| (2) Cetyl alcohol | 0.5 |
| (3) Beeswax | 2.0 |
| (4) Polyoxyethylene (20) monooleic ester | 1.0 |
| (5) Glyceryl monostearic ester. | 1.0 |
| (6) Ethanol | 3.0 |
| (7) Albutin | 10.0 |
| (8) Sodium bisulfite | 0.03 |
| (9) 1,3-butylene glycol | 5.0 |
| (10) Polyethylene glycol 400 | 2.0 |
| (11) Phellodendron bark extract (Production Ex. 3) | 1.0 |
| (12) Ion exchange water | Bal. |
| (13) Fragrance | 0.15 |
| (14) Methyl parabene | 0.3 |
| (15) Butyl parabene | 0.2 |
| (16) Thiourea | 0.1 |

Preparation Method

The ingredients (7), (9), (10), and (16) were added to the ingredient (12) and heated to dissolve and the resultant mixture held at 70° C. to form an aqueous phase. Further, the ingredient (11) was added to the ingredient (6) and dissolved to obtain an alcohol phase. On the other hand, the ingredients (1) to (5), (8), and (13) to (15) were mixed and heated to melt and held at 70° C. to obtain an oil phase. The oil phase was added to the aqueous phase and preemulsified, then the resultant mixture was homogeneously emulsified by a homomixer. The alcohol phase was added while stirring this. Thereafter, the stirring was continued and the mixture cooled down to 30° C. to obtain a milky lotion.

Example 10

Milky Lotion

| Ingredients | wt % |
|---|---|
| (1) Microcrystalline wax | 1.0 |
| (2) Beeswax | 1.0 |
| (3) Vaseline | 2.0 |
| (4) Liquid paraffin | 10.0 |
| (5) Squalane | 5.0 |
| (6) Jojoba oil | 5.0 |
| (7) Sorbitan sesquioleic ester | 4.0 |
| (8) Polyoxyethylene (20) sorbitanmonooleic ester | 1.0 |
| (9) Albutin | 5.0 |
| (10) Sodium bisulfite | 0.03 |
| (11) Tranexemic acid | 5.0 |
| (12) 1,3-butylene glycol | 5.0 |
| (13) Sorbitol | 2.0 |
| (14) Mulberry tree bark extract (Production Ex. 5) | 2.0 |
| (15) Bis-ethylhexyloxyphenol methoxyphenyltriazine | 1.5 |
| (16) Ion exchange water | Bal. |
| (17) Fragrance | 0.2 |
| (18) Ethyl parabene | 0.1 |
| (19) Butyl parabene | 0.1 |
| (20) Dibutyl hydroxytoluene | 0.05 |

Preparation Method

The ingredients (9) and (11) to (14) were added to the ingredient (16) and the resultant mixture heated and held at 70° C. to form an aqueous phase. On the other hand, the ingredients (1) to (8), (10), (15), and (17) to (20) were mixed and heated to melt and held at 70° C. to obtain an oil phase. While stirring the oil phase, the aqueous phase was gradually added to the oil phase and the resultant mixture homogeneously emulsified by a homomixer. After emulsification, the resultant mixture was cooled down to 30° C., while stirring vigorously to thereby obtain a milky lotion.

Example 11

Milky Lotion

| Ingredients | wt % |
|---|---|
| (1) Isopropyl alcohol | 10.0 |
| (2) Diglyceryl diisostearate | 0.5 |
| (3) POE modified dimethyl polysiloxane | 1.0 |
| (4) Octamethylcyclotetrasiloxane | 25.0 |
| (5) Decamethylcyclopentasiloxane | 15.0 |
| (6) Trimethylsiloxysilicic acid | 5.0 |
| (7) Eucalyptus oil | 3.0 |
| (8) Fragrance | 0.05 |
| (9) Dipropylene glycol | 2.0 |
| (10) *Houttuynia* extract (Production Ex. 1) | 0.5 |
| (11) Albutin | 7.0 |
| (12) Sodium bisulfite | 0.03 |
| (13) Methyl parabene | 0.1 |
| (14) Trisodium edetate | 0.1 |
| (15) Ion exchange water | Bal. |
| (16) Potassium chloride | 0.5 |

Preparation Method

The ingredients (1) to (8) were dissolved to obtain an oil phase, while the ingredients (9) to (16) were dissolved to obtain an aqueous phase. The aqueous phase was added to the oil phase obtained and emulsified to obtain a milky lotion.

Example 12

Milky Lotion

| Ingredients | wt % |
| --- | --- |
| A. Oil phase | |
| Dimethyl polysiloxane | 0.5 |
| Decamethylcyclopentasiloxane | 1.0 |
| Jojoba oil | 0.5 |
| B. Aqueous phase | |
| Albutin | 1.0 |
| *Houttuynia* extract (Production Ex. 1) | 0.5 |
| Alkyl-modified carboxyvinyl polymer | 0.05 |
| Carboxyvinyl polymer | 0.3 |
| Arabia gum | 0.05 |
| Ethyl alcohol | 8.0 |
| Trisodium edetate | 0.1 |
| Methyl parabene | 0.1 |
| Phenoxyethanol | 0.2 |
| Ion exchange water | Bal. |
| C. Neutral | |
| KOH | 0.15 |

Preparation Method

The phase obtained by dissolving the A phase (oil phase) ingredients was added to the phase obtained by dissolving the B phase (aqueous phase) ingredients and the resultant mixture emulsified. After the emulsification, the resultant mixture was neutralized by the C phase ingredient to obtain a milky lotion.

Example 13

Jelly

| Ingredients | wt % |
| --- | --- |
| (1) 95% ethanol | 10.0 |
| (2) Dipropylene glycol | 10.0 |
| (3) Glycerin | 5.0 |
| (4) Polyoxyethylene (15) oleyl alcohol ether | 2.0 |
| (5) Albutin | 0.5 |
| (6) Sodium bisulfite | 0.03 |
| (7) Distearate ascorbate | 0.5 |
| (8) Carboxyvinyl polymer ("Carbopol 942") | 1.0 |
| (9) Potassium hydroxide | 0.15 |
| (10) L-arginine | 0.1 |
| (11) *Houttuynia* extract (Production Ex. 2) | 2.0 |
| (12) Fragrance | 0.1 |
| (13) Phenoxyethanol | 0.4 |
| (14) Ion exchange water | Bal. |

Preparation Method

The ingredients (11), (5), (3), and (8) were homogeneously dissolved in the ingredient (14) to obtain an aqueous phase. On the other hand, the ingredients (2), (4), (6), (7), (12), and (13) were dissolved in the ingredient (1) and added to the aqueous phase. Next, the resultant mixture was neutralized by the ingredients (9) and (10) and thickened to obtain a jelly.

Example 14

Peel Off Pack

| Ingredients | wt % |
| --- | --- |
| Alcohol phase | |
| 95% ethanol | 10.0 |
| Polyoxyethylene (15) oleyl alcohol ether | 2.0 |
| Ethylhexyl triazone | 1.0 |
| Methyl parabene | 0.3 |
| Phenoxyethanol | 0.3 |
| Fragrance | 0.2 |
| Aqueous phase | |
| Rice bran extract (Production Ex. 4) | 1.0 |
| Albutin | 1.0 |
| Sodium bisulfite | 0.03 |
| Polyvinyl alcohol | 12.0 |
| Glycerin | 3.0 |
| Polyethylene glycol 1500 | 1.0 |
| Ion exchange water | Bal. |

Preparation Method

The aqueous phase ingredients were dissolved at 80° C. to prepare an aqueous phase which was then cooled to 50° C. Next, the alcohol phase ingredients were dissolved at room temperature to prepare an alcohol phase. This was added, then the resultant mixture homogeneously mixed and allowed to cool to obtain a peel off pack.

Example 15

Powder Pack

| Ingredients | wt % |
| --- | --- |
| Alcohol phase | |
| 95% ethanol | 5.0 |
| Methyl parabene | 0.1 |
| 1,2-pentadiol | 2.0 |
| Fragrance | 0.3 |
| Ascorbyl dioleate | 1.0 |
| Aqueous phase | |
| Rice bran extract (Production Ex. 4) | 5.0 |
| Albutin | 1.0 |
| Dipropylene glycol | 3.0 |
| Polyethylene glycol 1500 | 0.5 |
| Zinc oxide | 15.0 |
| Kaolin | 8.0 |
| Ion exchanged water | Bal. |

Preparation Method

A homogeneous aqueous phase was prepared from the aqueous phase ingredients at room temperature. To this was added an alcohol phase prepared from the alcohol ingredients at room temperature. The resultant mixture was homogeneously mixed to obtain a powder pack.

Example 16

Absorptive Ointment

| Ingredients | wt % |
| --- | --- |
| (1) Vaseline | 40.0 |
| (2) Stearyl alcohol | 18.0 |
| (3) Japan wax | 20.0 |
| (4) Polyoxyethylene (10) monooleic ester | 0.25 |
| (5) Glyceryl monostearic ester | 0.25 |
| (6) Placenta extract | 0.5 |
| (7) Japanese *coptis* extract (Production Ex. 6) | 3.0 |
| (8) Ion exchange water | Bal. |

Preparation Method

The ingredients (6) and (7) were added to the ingredient (8) and held at 70° C. to obtain an aqueous phase. On the other hand, the ingredients (1) to (5) were mixed and melted at 70° C. to obtain an oil phase. The oil phase was added to the aqueous phase and the resultant mixture homogeneously emulsified by a homomixer, then cooled to obtain an absorptive ointment.

Example 17

Peel Off Pack

| Ingredients | wt % |
| --- | --- |
| Aqueous phase | |
| Ion exchange water | Bal. |
| Glycerin | 5.0 |
| 1,3-butylene glycol | 2.0 |
| Ascorbic acid-2-glucoside | 1.0 |
| *Houttuynia* extract (Production Ex. 1) | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to the aqueous phase and the resultant mixture homogeneously mixed to obtain the cosmetic.

Example 18

Lotion

| Ingredients | wt % |
| --- | --- |
| Aqueous phase | |
| Ion exchange water | Bal. |
| Glycerin | 5.0 |
| Polyethylene glycol 400 | 2.0 |
| Xylitol | 0.5 |
| Ascorbic acid-2-glucoside | 1.0 |
| Phellodendron bark extract (Production Ex. 3) | 1.0 |
| Fast Green | 0.0003 |
| Metaphosphoric acid | 0.1 |
| Xanthan gum | 0.1 |
| Sodium alginate | 0.1 |
| Hyaluronic acid | 0.1 |
| Trimethylglycine | 3.0 |
| Potassium hydroxide | 0.4 |
| Sodium lactate | 0.1 |
| Lactic acid | 0.03 |
| Alcohol phase | |
| Ethanol (95%) | 7.0 |
| POE oleyl alcohol ether | 0.3 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to the aqueous phase and the resultant mixture homogeneously mixed to obtain the cosmetic.

Example 19

Lotion

| Ingredients | wt % |
| --- | --- |
| Water phase | |
| Ion exchange water | Bal. |
| Glycerin | 5.0 |
| 1,3-butylene glycol | 2.0 |
| Ascorbic acid-2-glucoside | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| *Houttuynia* extract (Production Ex. 1) | 0.01 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to the aqueous phase and the resultant mixture homogeneously mixed to obtain the cosmetic.

Example 20

Lotion

| Ingredients | wt % |
|---|---|
| Aqueous phase | |
| Ion exchange water | Bal. |
| Glycerin | 5.0 |
| 1,3-butylene glycol | 2.0 |
| Ascorbic acid-2-glucoside | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Wild rose extract (Production Ex. 11) | 0.01 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to and homogeneously mixed with the aqueous phase.

Example 21

Lotion

| Ingredients | wt % |
|---|---|
| Aqueous phase | |
| Ion exchange water | Bal. |
| Glycerin | 5.0 |
| 1,3-butylene glycol | 2.0 |
| Ascorbic acid-2-glucoside | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Thyme extract (Production Ex. 7) | 0.5 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to and homogeneously mixed with the aqueous phase.

Example 22

Lotion

| Ingredients | wt % |
|---|---|
| Aqueous phase | |
| Ion exchange water | Bal. |
| Glycerin | 5.0 |
| 1,3-butylene glycol | 2.0 |
| Ascorbic acid-2-glucoside | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Balm mint extract (Production Ex. 12) | 0.01 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to and homogeneously mixed with the aqueous phase.

Example 23

Lotion

| Ingredients | wt % |
|---|---|
| Aqueous phase | |
| Ion exchange water | Bal. |
| Glycerin | 5.0 |
| 1,3-butylene glycol | 2.0 |
| Ascorbic acid-2-glucoside | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Peach seed extract (Production Ex. 8) | 0.01 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to and homogeneously mixed with the aqueous phase.

Example 24

Lotion

| Ingredients | wt % |
|---|---|
| Aqueous phase | |
| Ion exchange water | Bal. |
| Glycerin | 5.0 |
| 1,3-butylene glycol | 2.0 |
| Ascorbic acid-2-glucoside | 1.0 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Nettle extract (Production Ex. 9) | 0.01 |
| Vitamin E acetate | 0.05 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to and homogeneously mixed with the aqueous phase.

Example 25

Lotion

| Ingredients | wt % |
|---|---|
| Aqueous phase | |
| Ion exchange water | Bal. |
| Glycerin | 5.0 |
| 1,3-butylene glycol | 2.0 |
| Ascorbic acid-2-glucoside | 1.0 |
| Calendula extract (Production Ex. 10) | 0.01 |
| Brilliant Blue | 0.0002 |
| Edetic acid salt | 0.1 |
| Potassium hydroxide | 0.2 |
| Sodium citrate | 0.15 |
| Citric acid | 0.03 |
| Alcohol phase | |
| Ethanol (95%) | 7.0 |
| Polyoxyethylene (60) hydrogenated castor oil ether | 0.3 |
| Vitamin E acetate | 0.1 |
| Fragrance | 0.05 |
| Methyl parabene | 0.15 |
| Phenoxyethanol | 0.3 |

Preparation Method

The aqueous phase ingredients and the alcohol ingredients were respectively homogeneously dissolved, then the alcohol phase was added to and homogeneously mixed with the aqueous phase.

Example 26

Milky Lotion

| | Ingredients | wt % |
|---|---|---|
| (1) | Isopropyl alcohol | 10.0 |
| (2) | Diglyceryl diisostearate | 0.5 |
| (3) | POE modified dimethyl polysiloxane | 1.0 |
| (4) | Octamethylcyclotetrasiloxane | 25.0 |
| (5) | Decamethylcyclopentasiloxane | 15.0 |
| (6) | Trimethylsiloxysilicic acid | 5.0 |
| (7) | Eucalyptus oil | 3.0 |
| (8) | Fragrance | 0.05 |
| (9) | Dipropylene glycol | 2.0 |
| (10) | Thyme extract (Production Ex. 7) | 0.01 |
| (11) | Albutin | 7.0 |
| (12) | Sodium bisulfite | 0.03 |
| (13) | Methyl parabene | 0.1 |
| (14) | Trisodium edetate | 0.1 |
| (15) | Ion exchange water | Bal. |
| (16) | Potassium chloride | 0.5 |

Preparation Method

The ingredients (1) to (8) were dissolved (oil phase), the ingredients (9) to (16) were dissolved (aqueous phase), the aqueous phase was added to the oil phase, and the resultant mixture was emulsified to obtain a milky lotion.

Example 27

Milky Lotion

| | Ingredients | wt % |
|---|---|---|
| (1) | Isopropyl alcohol | 10.0 |
| (2) | Diglyceryl diisostearate | 0.5 |
| (3) | POE modified dimethyl polysiloxane | 1.0 |
| (4) | Octamethylcyclotetrasiloxane | 25.0 |
| (5) | Decamethylcyclopentasiloxane | 15.0 |
| (6) | Trimethylsiloxysilicic acid | 5.0 |
| (7) | Eucalyptus oil | 3.0 |
| (8) | Fragrance | 0.05 |
| (9) | Dipropylene glycol | 2.0 |
| (10) | Thyme extract (Production Ex. 7) | 0.01 |
| (11) | Albutin | 7.0 |
| (12) | Sodium bisulfite | 0.03 |
| (13) | Methyl parabene | 0.1 |
| (14) | Trisodium edetate | 0.1 |
| (15) | Ion exchange water | Bal. |
| (16) | Potassium chloride | 0.5 |

Preparation Method

The ingredients (1) to (8) were dissolved (oil phase), the ingredients (9) to (16) were dissolved (aqueous phase), the aqueous phase was added to the oil phase, and the resultant mixture was emulsified to obtain a milky lotion.

Example 28

Milky Lotion

| | Ingredients | wt % |
|---|---|---|
| (1) | Isopropyl alcohol | 10.0 |
| (2) | Diglyceryl diisostearate | 0.5 |
| (3) | POE modified dimethyl polysiloxane | 1.0 |

-continued

| | Ingredients | wt % |
|---|---|---|
| (4) | Octamethylcyclotetrasiloxane | 25.0 |
| (5) | Decamethylcyclopentasiloxane | 15.0 |
| (6) | Trimethylsiloxysilicic acid | 5.0 |
| (7) | Eucalyptus oil | 3.0 |
| (8) | Fragrance | 0.05 |
| (9) | Dipropylene glycol | 2.0 |
| (10) | Peach seed extract (Production Ex. 8) | 0.03 |
| (11) | Albutin | 7.0 |
| (12) | Sodium bisulfite | 0.03 |
| (13) | Methyl parabene | 0.1 |
| (14) | Trisodium edetate | 0.1 |
| (15) | Ion exchange water | Bal. |
| (16) | Potassium chloride | 0.5 |

Preparation Method

The ingredients (1) to (8) were dissolved (oil phase), the ingredients (9) to (16) were dissolved (aqueous phase), the aqueous phase was added to the oil phase, and the resultant mixture was emulsified to obtain a milky lotion.

Example 29

Milky Lotion

| | Ingredients | wt % |
|---|---|---|
| (1) | Isopropyl alcohol | 10.0 |
| (2) | Diglyceryl diisostearate | 0.5 |
| (3) | POE modified dimethyl polysiloxane | 1.0 |
| (4) | Octamethylcyclotetrasiloxane | 25.0 |
| (5) | Decamethylcyclopentasiloxane | 15.0 |
| (6) | Trimethylsiloxysilicic acid | 5.0 |
| (7) | Eucalyptus oil | 3.0 |
| (8) | Fragrance | 0.05 |
| (9) | Dipropylene glycol | 2.0 |
| (10) | Calendula extract (Production Ex. 10) | 0.3 |
| (11) | Albutin | 7.0 |
| (12) | Sodium bisulfite | 0.03 |
| (13) | Methyl parabene | 0.1 |
| (14) | Trisodium edetate | 0.1 |
| (15) | Ion exchange water | Bal. |
| (16) | Potassium chloride | 0.5 |

Preparation Method

The ingredients (1) to (8) were dissolved (oil phase), the ingredients (9) to (16) were dissolved (aqueous phase), the aqueous phase was added to the oil phase, and the result and mixture was emulsified to obtain a milky lotion.

Example 30

Milky Lotion

| | Ingredients | wt % |
|---|---|---|
| (1) | Isopropyl alcohol | 10.0 |
| (2) | Diglyceryl diisostearate | 0.5 |
| (3) | POE modified dimethyl polysiloxane | 1.0 |
| (4) | Octamethylcyclotetrasiloxane | 25.0 |
| (5) | Decamethylcyclopentasiloxane | 15.0 |
| (6) | Trimethylsiloxysilicic acid | 5.0 |
| (7) | Eucalyptus oil | 3.0 |
| (8) | Fragrance | 0.05 |

-continued

| | Ingredients | wt % |
|---|---|---|
| (9) | Dipropylene glycol | 2.0 |
| (10) | Wild rose extract (Production Ex. 11) | 1.0 |
| (11) | Albutin | 7.0 |
| (12) | Sodium bisulfite | 0.03 |
| (13) | Methyl parabene | 0.1 |
| (14) | Trisodium edetate | 0.1 |
| (15) | Ion exchange water | Bal. |
| (16) | Potassium chloride | 0.5 |

Preparation Method

The ingredients (1) to (8) were dissolved (oil phase), the ingredients (9) to (16) were dissolved (aqueous phase), the aqueous phase was added to the oil phase, and the resultant mixture was emulsified to obtain a milky lotion.

Example 31

Milky Lotion

| | Ingredients | wt % |
|---|---|---|
| (1) | Isopropyl alcohol | 10.0 |
| (2) | Diglyceryl diisostearate | 0.5 |
| (3) | POE modified dimethyl polysiloxane | 1.0 |
| (4) | Octamethylcyclotetrasiloxane | 25.0 |
| (5) | Decamethylcyclopentasiloxane | 15.0 |
| (6) | Trimethylsiloxysilicic acid | 5.0 |
| (7) | Eucalyptus oil | 3.0 |
| (8) | Fragrance | 0.05 |
| (9) | Dipropylene glycol | 2.0 |
| (10) | Balm mint extract (Production Ex. 12) | 0.02 |
| (11) | Albutin | 7.0 |
| (12) | Sodium bisulfite | 0.03 |
| (13) | Methyl parabene | 0.1 |
| (14) | Trisodium edetate | 0.1 |
| (15) | Ion exchange water | Bal. |
| (16) | Potassium chloride | 0.5 |

Preparation Method

The ingredients (1) to (8) were dissolved (oil phase), the ingredients (9) to (16) were dissolved (aqueous phase), the aqueous phase was added to the oil phase, and the resultant mixture was emulsified to obtain a milky lotion.

The cosmetic compositions of the present invention containing the hair growth inhibitors having herbs as active ingredients of the above embodiments were all observed to have superior hair growth inhibitor effects in the tests on their effects.

INDUSTRIAL APPLICABILITY

As explained in detail above, the hair growth inhibitor of the present invention having as an active ingredient a herb selected from *phellodendron, houttuynia*, rice bran, mulberry tree bark, Japanese *coptis*, thyme, peach seed, nettle, *calendula*, wild rose, and balm mint or the extract thereof has a superior hair growth inhibiting ability and is high in safety, in particular is high in safety to the human body. It can be used formulated into a drug, quasi-drug, cosmetic, or various other compositions to be applied to the skin. These compositions can exhibit superior hair growth inhibiting capability. In particular, when formulated in a cosmetic, it is possible to provide a cosmetic having a superior hair growth inhibiting activity and having a high safety. More specifically, it becomes possible to provide a cosmetic which features less irritation to the skin and can lighten more the burden of the work of treatment for removing body hair.

The invention claimed is:

1. A method for inhibiting hair growth comprising:
 administering a therapeutically effective amount of a topical formulation including at least one herb extract selected from the group consisting of (i) herb extracts of above-ground parts of *Houttuynia* (*Houttuynia cordata* Thunb.), in the flowering season with an extracting solvent and (ii) herb extracts of root and stem of Japanese *Coptis* (*Coptis japonica* Makino),
 wherein the at least one herb extract is prepared by extracting the *Houttuynia* and the Japanese *Coptis* with an extracting solvent wherein the extracting solvent is independently one or more of water, methanol, ethanol, propylene glycol, 1,3-butylene glycol, glycerin, aqueous alcohols, chloroform, dichloroethane, carbon tetrachloride, acetone, ethyl acetate, and hexane.

2. A method for inhibiting hair growth according to claim 1 including a base agent.

3. A method for inhibiting hair growth as claimed in claim 2, wherein a formulating amount of said extract is, 0.000001 to 5% by weight, in term of dry weight, based upon the total weight of the topical formulation.

4. A method for inhibiting hair growth as claimed in claim 2, wherein the topical formulation is a cosmetic composition.

5. A method for inhibiting hair growth as claimed in claim 4, wherein the cosmetic composition is at least one member selected from the group consisting of a hair removal agent, depilatory agent, shaving agent, shaving pre-treatment agent, shaving after-treatment agent, hair removal after-treatment agent and depilatory after-treatment agent.

6. A method for inhibiting hair growth as claimed in claim 3, wherein the topical formulation is a cosmetic composition.

7. A method for inhibiting hair growth as claimed in claim 6, wherein the cosmetic composition is at least one member selected from the group consisting of a hair removal agent, depilatory agent, shaving agent, shaving pre-treatment agent, shaving after-treatment agent, hair removal after-treatment agent and depilatory after-treatment agent.

* * * * *